US007959942B2

(12) United States Patent
Cottone

(10) Patent No.: US 7,959,942 B2
(45) Date of Patent: *Jun. 14, 2011

(54) BIOABSORBABLE MEDICAL DEVICE WITH COATING

(75) Inventor: Robert J. Cottone, Davie, FL (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 257 days.

This patent is subject to a terminal disclaimer.

(21) Appl. No.: 11/875,887

(22) Filed: Oct. 20, 2007

(65) Prior Publication Data

US 2008/0097575 A1 Apr. 24, 2008

Related U.S. Application Data

(60) Provisional application No. 60/862,409, filed on Oct. 20, 2006.

(51) Int. Cl.
*A61F 2/00* (2006.01)
*A61F 2/06* (2006.01)
*A61B 17/04* (2006.01)

(52) U.S. Cl. ..... 424/428; 424/426; 424/423; 424/130.1; 623/1.13; 623/1.38; 623/1.42; 623/1.47; 606/230

(58) Field of Classification Search ........................ None
See application file for complete search history.

(56) References Cited

U.S. PATENT DOCUMENTS

| | | | |
|---|---|---|---|
| 5,066,772 A | 11/1991 | Tang | |
| 5,085,629 A | 2/1992 | Goldberg et al. | |
| 5,317,064 A | 5/1994 | Spinu | |
| 5,320,624 A | 6/1994 | Kaplan et al. | |
| 5,531,998 A | 7/1996 | Mares et al. | |
| 5,716,396 A | 2/1998 | Williams, Jr. | |
| 5,776,161 A | 7/1998 | Globerman | |
| 5,827,322 A | 10/1998 | Williams | |
| 5,925,061 A | 7/1999 | Ogi | |
| 5,948,016 A | 9/1999 | Jang | |
| 5,964,798 A | 10/1999 | Imran | |
| 6,001,395 A | 12/1999 | Coombes et al. | |
| 6,033,394 A | 3/2000 | Vidlund et al. | |
| 6,033,433 A | 3/2000 | Ehr | |
| 6,110,164 A | 8/2000 | Vidlund | |
| 6,245,103 B1 | 6/2001 | Stinson | |
| 6,251,134 B1 | 6/2001 | Alt et al. | |
| 6,254,632 B1 | 7/2001 | Wu et al. | |
| 6,258,382 B1 | 7/2001 | Takaoka et al. | |
| 6,312,458 B1 | 11/2001 | Golds | |
| 6,338,739 B1 | 1/2002 | Datta et al. | |
| 6,365,173 B1 | 4/2002 | Domb | |
| 6,511,505 B2 | 1/2003 | Cox | |
| 6,537,284 B1 | 3/2003 | Inoue | |
| 6,575,888 B2 | 6/2003 | Zamora et al. | |
| 6,585,755 B2 | 7/2003 | Jackson et al. | |
| 6,599,314 B2 | 7/2003 | Mathis | |
| 6,607,548 B2 * | 8/2003 | Pohjonen et al. ............. | 606/230 |
| 6,623,521 B2 | 9/2003 | Steinke et al. | |
| 6,652,575 B2 | 11/2003 | Wang et al. | |
| 6,652,579 B1 | 11/2003 | Cox et al. | |
| 6,730,116 B1 | 5/2004 | Wolinsky | |
| 6,770,729 B2 | 8/2004 | Van Antwerp | |
| 6,805,706 B2 | 10/2004 | Solovay et al. | |
| 6,896,697 B1 | 5/2005 | Yip et al. | |
| 7,001,328 B1 * | 2/2006 | Barofsky et al. ............. | 600/36 |
| 7,070,607 B2 | 7/2006 | Murayama et al. | |
| 7,326,245 B2 | 2/2008 | Rosenthal | |
| 2002/0007212 A1 | 1/2002 | Brown et al. | |
| 2002/0111671 A1 | 8/2002 | Stenzel | |
| 2002/0188347 A1 | 12/2002 | Mathis | |
| 2003/0149474 A1 | 8/2003 | Becker | |
| 2003/0212449 A1 | 11/2003 | Cox | |
| 2003/0229393 A1 * | 12/2003 | Kutryk et al. ............. | 623/1.46 |
| 2004/0039441 A1 * | 2/2004 | Rowland et al. ............. | 623/1.42 |
| 2004/0088044 A1 | 5/2004 | Brown | |
| 2004/0098090 A1 | 5/2004 | Williams | |
| 2004/0167572 A1 | 8/2004 | Roth et al. | |
| 2004/0249442 A1 | 12/2004 | Fleming | |
| 2005/0107864 A1 | 5/2005 | Hong et al. | |
| 2005/0271701 A1 * | 12/2005 | Cottone et al. ............. | 424/426 |
| 2005/0288771 A1 | 12/2005 | Majercak | |
| 2006/0004437 A1 | 1/2006 | Jayaraman | |
| 2006/0035854 A1 | 2/2006 | Goldstein et al. | |
| 2006/0188486 A1 | 8/2006 | Carpenter et al. | |

(Continued)

FOREIGN PATENT DOCUMENTS

EP 0600237 A1 6/1994

(Continued)

OTHER PUBLICATIONS

Grabow, et al. "Mechanical Properties of a Biodegradable Balloon-expandable Stent from Poly(L-lactide) for Peripheral Vascular Applications," Journal of Medical Devices. 2007, vol. 1; pp. 84-88.

Columbo, et al. "The bioabsorbable stent as a virtual prosthesis," The Lancet. 2009, vol. 373; pp. 869-870.

International Preliminary Report on Patentability for international application No. PCT/US07/74050 issued by the International Preliminary Examining Authority mailed on Jul. 21, 2009.

Written Opinion for the International Application No. PCT/US07/82034 issued by the International Preliminary Examining Authority mailed on Jan. 19, 2010.

International Search Report dated, Jun. 17, 2008 for, PCT Application No. PCT/US2007/082034 International Filing Date Oct. 20, 2007.

Yuancai Dong, Si-Shen Feng, Nanoparticles of poly(D,L-lactide)/methoxy poly(ethylene glycol)-poly(D,L-lactide) blends for controlled release of paclitaxel. Journal of Biomedical Materials Research Part A. vol. 78A, Issue 1, pp. 12-19. Apr. 2006.

(Continued)

*Primary Examiner* — Christine J Saoud
*Assistant Examiner* — Jegatheesan Seharaseyon
(74) *Attorney, Agent, or Firm* — Michael A. Davitz

(57) ABSTRACT

A biodegradable, bioabsorbable medical device with a coating for capturing progenitor endothelial cells in vivo and delivering a therapeutic agent at the site of implantation. The coating on the medical device is provided with a biabsorbable polymer composition such as a bioabsorbable polymer, copolymer, or terpolymer, and a copolymer or terpolymer additive for controlling the rate of delivery of the therapeutic agent.

29 Claims, 5 Drawing Sheets

U.S. PATENT DOCUMENTS

| | | |
|---|---|---|
| 2006/0265048 A1 | 11/2006 | Cheng |
| 2007/0032857 A1 | 2/2007 | Schmid |
| 2007/0043426 A1 | 2/2007 | Abbate |
| 2007/0135578 A1 | 6/2007 | Mather |
| 2007/0233232 A1 | 10/2007 | St. Germain |
| 2008/0051866 A1 | 2/2008 | Chen |
| 2008/0051868 A1 | 2/2008 | Cottone |
| 2008/0051873 A1 | 2/2008 | Cottone |
| 2008/0051874 A1 | 2/2008 | Cottone |
| 2008/0051875 A1 | 2/2008 | Cottone |
| 2008/0097575 A1 | 4/2008 | Cottone |
| 2008/0097576 A1 | 4/2008 | Cottone |
| 2008/0118546 A1 | 5/2008 | Thatcher |
| 2008/0206440 A1 | 8/2008 | Cottone |
| 2009/0281249 A1 | 11/2009 | Thatcher |
| 2010/0003327 A1 | 1/2010 | Thatcher |

FOREIGN PATENT DOCUMENTS

| | | |
|---|---|---|
| EP | 01737387 | 10/2005 |
| EP | 1681035 A1 | 7/2006 |

OTHER PUBLICATIONS

Zhang et al. "Preparation of Linear Low-Density Polyethylene by the in Situ Copolymerization of Ethylene with an Iron Oligomerization Catalyst and rac-Ethylene bis(indenyl) Zirconium (IV) Dichloride," Journal of Polymer Science: Part A: Polymer Chemistry, 2005, vol. 43; pp. 984-993.

* cited by examiner

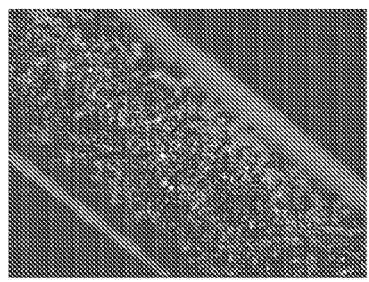 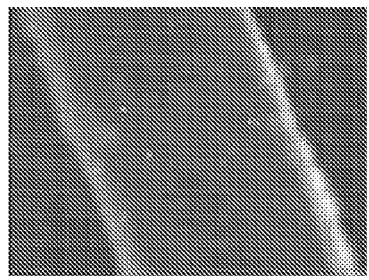 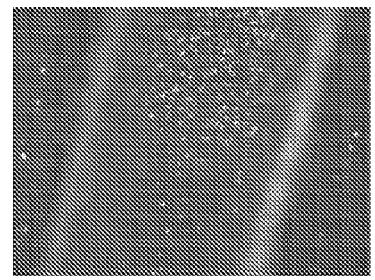
FIG. 3　　　　FIG. 4　　　　FIG. 5
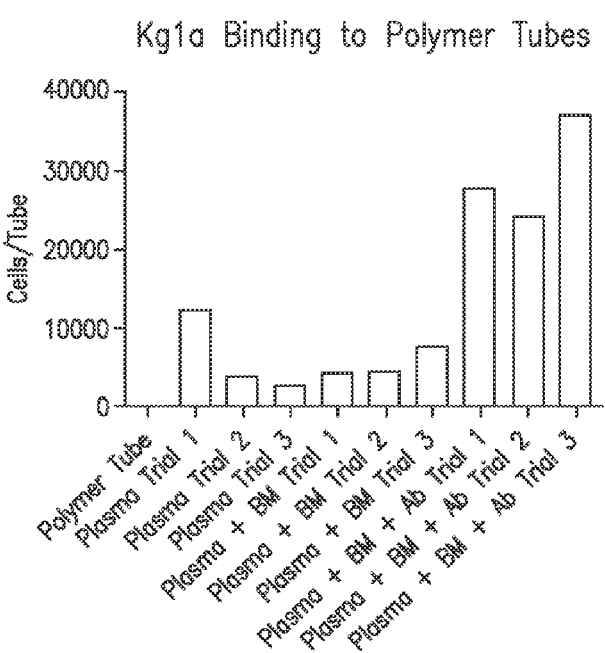
FIG. 6

BIOABSORBABLE MEDICAL DEVICE WITH COATING

CROSS-REFERENCE TO RELATED APPLICATION

This Application claims benefit of U.S. Provisional Patent Application Ser. No. 60/862,409, filed on Oct. 20, 2006.

BACKGROUND

All references cited in this specification, and their references, are incorporated by reference herein in their entirety where appropriate for teachings of additional or alternative details, features, and/or technical background.

The invention relates in embodiments disclosed herein to a novel medical device with a coating. Such device may be configured for implantation into vessels or luminal structures within the body. More particularly, the present invention in embodiments relates to stents and synthetic grafts which are coated with a controlled-release matrix comprising a medicinal substance for direct delivery to the surrounding tissues, and a ligand attached thereto for capturing progenitor endothelial cells that may be found in the bodily fluids contacting the matrix (e.g., blood-contacting surface). The captured cells may result in the formation of mature endothelium at site of injury. In particular, a polymer matrix/drug/ligand-coated stent may be used, for example, in therapy of diseases such as restenosis, artherosclerosis, and endoluminal reconstructive therapies.

A medical device of embodiments of the present invention may comprise a polymer composition comprising a base material formed from, or including, a bioabsorbable polymer, copolymer, or terpolymer. The base material may further comprise a copolymer or terpolymer additive. One advantageous base material allows for a "soft" breakdown mechanism allowing for the breakdown of the component polymers to be less injurious to the surrounding tissue.

A persistent problem associated with the use of metallic devices such as stents in treating cardiovascular disease is the formation of scar tissue coating of the stent at the site of implantation the so-called process of restenosis. Moreover, metallic or polymeric non-absorbable stents may prevent vascular lumen remodeling and expansion. Numerous approaches have been tried to prevent scar tissue, and reduce complement activation of the immune response, which may be attendant to such implanted devices. Furthermore, an advantageous implant with a reduced inflammatory response and lower potential for trauma upon break-up of an implant and/or its component materials may be desired. A desirable improvement target may be found in the need for increased flexibility of shane and structure of medical devices for implantation, particularly into blood vessels.

Reference is made to U.S. Pat. No. 6,607,548 B2 (Inion), issued Aug. 19, 2003, which discloses compositions that are biocompatible and bioresorbable using a lactic acid or glycolic acid based polymer or copolymer blended with one or more copolymer additives. As a result, implants made from these blends are said to be cold-bendable without crazing or cracking. EP 0401844 discloses a blend of Poly-L-lactide with Poly D-DL-lactide.

It may be argued that bioabsorbable medical devices (such as stents) may be more suitable in the treatment of vascular disease than non-bioabsorbable medical devices. For example, it is known that non-biodegrable metallic stents can induce thrombosis by irritation of the blood vessel after since they are permanently embedded in the blood vessel. Further, their mechanical properties may deteriorate impairing blood vessel properties.

Coated medical devices are available commercially and approved by the FDA. For example, drug eluting stents containing anti-cancer drugs such as rapamycin and paclitaxel are commonly implanted into coronary arteries and have become the preferred method for used in percutaneous coronary interventions, because of their significant ability to reduce restenosis rates. One limitation of drug eluting stents has been that the patient needs to take supplemental oral drugs, such as aspirin and clopidrogel to prevent thrombosis from occurring at an early stage after implantation. Furthermore, the polymers used as a vehicle for drug delivery in some devices may induce vessel irritation, endothelial cell dysfunction, vessel hypersensitivity and chronic inflammation at the site of stent implantation (Waksman 2006).

The present inventors have recognized that it may be advantageous to develop a compatible polymer blends for medical devices, such as stents and vascular synthetic grafts, which provide a toughening mechanism to the base polymer when deployed into the body. In one embodiment, the base polymer composition may be used to impart additional molecular free volume to the base polymer to affect molecular motion sufficiently to allow for re-crystallization to occur at physiological conditions, for example, upon the addition of molecular strain in deployment. They have further recognized that increased molecular free volume can also increase the rate of water uptake adding both a plasticizing effect as well as increasing the bulk degradation kinetics. The composition may be formulated to allow for a "soft" breakdown mechanism such that the breakdown proceeds while being friendly to the surrounding tissue (less inflammatory response, and rendering lower potential for trauma upon break up of an implant). By selecting a polymer or copolymer for either the base or the additive or both, an enhanced hydrophilic property of the polymer blend may reduce complement activation and minimize or prevent opsonization. (see Dong and Feng, J of Biomedical Materials Research part A DOI 10.1002, 2006).

SUMMARY

Disclosed in embodiments herein are biodegradable, bioabsorbable medical devices with a coating for the treatment or amelioration of various diseases, including vascular disease, and conditions in particular, artherosclerosis and/or restenosis.

In one embodiment, the medical device comprises a device for implantation into a patient for the treatment of disease. The medical device comprises a bioabsorbable, biodegradable material, which may be a polymer of synthetic or natural origin, which has the ability to undergo deformation when employed in vivo, for example, from a solid or rigid state during manufacture to a flexible and pliable material after implantation in vivo, yet in its pliable form is capable of maintaining the desired blood vessel diameter upon deployment in situ.

In one embodiment, the medical device comprises a polymer composition and/or formulation, comprising: a polymer such as a poly(L-lactide), or a poly(D-lactide) as the base polymer, or copolymers thereof and wherein modifying copolymers including, poly L(or D)-lactide-co-Tri-methylene-carbonate and poly L(or D)-lactide-co-ε-caprolactone can be used to link the base polymers. These copolymers can be synthesized as block copolymers or as "blocky" random copolymers wherein the lactide chain length is sufficiently long enough to crystallize. Such polymer compositions may allow the development of a crystal morphology that can enhance the mechanical properties of the medical device; enhance processing conditions, and provide potential of cross moiety crystallization, for example, thermal cross-links. In this embodiment, the polymer composition allows the development of the lactide racemate crystal structure, between the L and D moieties, to further enhance the mechanical properties of the medical device.

In another embodiment, the medical device may comprise a polymer composition wherein the properties of the polymer composition can be engineered to produce a desired degradation time of the base polymer so that the degradation time can be predicted after implantation of the device. For example, the medical device can comprise base polymers having enhanced degradation kinetics. In this manner, the degradation time of the base polymer can be shortened. For example, the starting material used as base polymer can be a lower molecular weight composition and/or a base polymer that is more hydrophilic or liable to hydrolytic chain scission.

In another embodiment, medical device can comprise a polymer composition which comprises a base copolymer wherein one polymer moiety is sufficiently long enough and not sterically hindered to crystallize, such as L-lactide or D-lactide with a lesser or shorter polymer moiety, for example Glycolide or Polyethylene Glycol (PEG), or monomethoxy-terminated PEG (PEG-MNE).

In another embodiment, compositions in addition to the base polymer, the modifying polymer or co-polymer may also have enhanced degradation kinetics such as with an e-caprolactone copolymer moiety wherein the caprolactone remains amorphous with resulting segments more susceptible to hydrolysis.

In another embodiment, the composition can incorporate PEG copolymers, for example either AB diblock or ABA triblock with the PEG moiety being approximately 1%. In this embodiment, the mechanical properties of the Lactide (see Enderlie and Buchholz SFB May 2006) are maintained. In this embodiment the incorporation of either PEG or PEG-MME copolymers may also be used to facilitate drug attachment to the polymer, for example in conjunction with a drug eluding medical device.

In one embodiment, the polymer compositions are used to manufacture medical device for implantation into a patient. The medical devices which may have biodegradable, bioabsorbable properties as discussed above, may include, but are not limited to stents, stent grafts, vascular synthetic grafts, catheters, vascular shunts, valves and the like.

The coating on the medical device of embodiments of the present invention can comprise a bioabsorbable, biodegradable matrix comprising a synthetic or naturally occurring polymer, or non-polymer material, which can be applied to the medical device, and can comprise similar base polymers as the medical device. The coating on the medical device can further comprise a biological and/or pharmaceutical substance, for example, drugs for delivery to the adjacent tissues where device is implanted into the body. The coating may also include a radiopaque material to allow for easier identification of the medical device when placed in the body. Such drug or pharmaceutical substances or radioopaque materials may be bound to the matrix, for example, by reaction of such materials and substances with end groups of a polymer comprising the matrix, other chemical linkage (such as through linkers associated with the polymer), by simple mixing (localized or dispersed) of the materials and substances into the matrix, and other methods known in the art. Such coating may be applied to the medical device itself, or may be applied to material or fabrication from which the medical device is made—for example applied to a tube structure from which a stent is cut (e.g. by laser cutting, photolasing, physical or air knife, etc.).

In another embodiment, the invention is directed to a method of coating a medical device with the a bioabsorbable coating composition, comprising applying one or more layers of a matrix such as a biobsorbable polymer matrix to the medical device. Coatings at different portions of the medical device may be the same or different. For example in a stent, the coating located on the outer surface of the stent may be different than the coating on the inner section of the stent. Further, the number of layers of coating on the outer surface of the stent might be different from the number of layers of coating on the inside of the stent. For example, the inner surface of a stent may have coating that breaks down slower than the coating on the outside of the stent, or have additional materials, or layers, associated therewith, for example a ligand that captures cells, than the outer surface (which may for example have drug eluting layer). Alternatively, or additionally, the inner layer may have a different drug or biological ligand associated therewith than the outer layer. Of course, the inner and outer coatings may be similar or identical to one another in terms of pharmacological/biological effect.

In one embodiment, an implantable medical device is provided, comprising a crystallizable polymer composition and a coating; said medical device comprising, a base polymer linked with a modifying copolymer in the form of block copolymer or blocky random copolymers, wherein the polymer chain length is sufficiently long enough to allow crossmoiety crystallization; and said coating comprising a bioabsorbable matrix and a ligand. In this embodiment, the ligand is configured to bind target cells in vivo. The ligand can be a small molecule, a peptide, an antibody, antibody fragments, or combinations thereof and the target cell is a progenitor endothelial cell antigen. In certain embodiments, the coating comprises one or more layers, and can comprise a matrix comprising naturally occurring or synthetic biodegradable polymer. In this embodiment, matrix can comprise at least one of the group consisting of: tropoelastin, elastin, laminin, fibronectin, basement membrane proteins, and cross-linked tropoelastin.

In one embodiment, the implantable medical device comprises a coating wherein at least one coating layer, or the implantable medical device itself, comprises a radioopaque or radio-detectable material. The radio-opaque material can be for example, tantalum, iodine, and the like, which can be detected or imaged by X-ray techniques. In some embodiments, the implantable medical device can be impregnated with a pharmacological or biological substance. In this embodiment, the radio-opaque material can be blended with the pharmaceutical substance or a biological substance and the base polymers and or attached to the polymer structure during manufacturing.

In alternate embodiments, the implantable medical device can comprise a tube defining a lumen, said tube having an outer surface and an inner surface, said inner surface surrounding said lumen, wherein the outer surface can be coated with a composition comprising a pharmacological substance. In some embodiments, the outer or inner surface can be coated with a composition comprising a biological substance. In one embodiment, the pharmacological substance is at least one of the group consisting of: cyclosporin A, mycophenolic acid, mycophenolate mofetil acid, rapamycin, rapamycin derivatives, biolimus A9, CCI-779, RAD 001, AP23573, azathioprene, pimecrolimus, tacrolimus (FK506), tranilast, dexamethasone, corticosteroid, everolimus, retinoic acid, vitamin E, rosglitazone, simvastatins, fluvastatin, estrogen, 17β- estradiol, hydrocortisone, acetaminophen, ibuprofen, naproxen, fluticasone, clobetasol, adalimumab, sulindac, dihydroepiandrosterone, testosterone, puerarin, platelet factor 4, basic fibroblast growth factor, fibronectin, butyric acid, butyric acid derivatives, paclitaxel, paclitaxel derivatives, LBM-642, deforolimus, and probucol.

In embodiments comprising a biological substance, the biological substance is at least one of the group consisting of: antibiotics/antimicrobials, antiproliferative agents, antineoplastic agents, antioxidants, endothelial cell growth factors, smooth muscle cell growth and/or migration inhibitors, thrombin inhibitors, immunosuppressive agents, anti-platelet aggregation agents, collagen synthesis inhibitors, therapeutic antibodies, nitric oxide donors, antisense oligonucleotides, wound healing agents, therapeutic gene transfer constructs, peptides, proteins, extracellular matrix components, vasodialators, thrombolytics, anti-metabolites, growth factor agonists, antimitotics, steroids, steroidal antiinflammatory agents, chemokines, proliferator-activated receptor-gamma agonists, proliferator-activated receptor-alpha agonists proliferator-activated receptor-beta agonists, proliferator-activated receptor-alpha/beta agonists, proliferator-activated receptor-delta agonists, NFκβ, proliferator-activated receptor-alpha-gamma agonists, nonsterodial antiinflammatory agents, angiotensin converting enzyme(ACE) inhibitors, free radical scavengers, inhibitors of the CX3CR1 receptor and anti-cancer chemotherapeutic agents.

In one embodiment, the implantable medical device can comprise a crystallizable bioabsorbable polymer composition comprises a base polymer of from about 70% by weight of poly (L-lactide) with 30% by weight of modifying copolymer poly L-lactice-co-TMC.

In some embodiments, a bioabsorbable implant is provided comprising: a crystallizable composition comprising a base polymer of poly L-lactide or poly D-lactide linked with modifying copolymers comprising poly L(or D)-lactide-co-Trimethylene-carbonate or poly L(or D)-lactide-co-ε-caprolactone in the form of block copolymers or as blocky random copolymers wherein the lactide chain length is sufficiently long enough to allow cross-moiety crystallization; and a ligand. In this embodiments, the bioabsorbable implant can have a base polymer composition blend of 70% by weight of poly L-lactide with 30% by weight of modifying copolymer poly L-lactice-co-TMC.

In embodiments herein, the bioabsorbable implant comprises a ligand which can be a small molecule, a peptide, an antibody, antibody fragments, or combinations thereof and the target cell is a progenitor endothelial cell. In this embodiment, the bioabsorbable an antibody or antibody fragments is specific for binding a progenitor endothelial cell membrane antigen. The antibodies can bind to progenitor endothelial cell membrane antigen and can be selected from the group consisting of CD34, CD45, CD133, CD14, CDw90, CD117, HLA-DR, VEGFR-1, VEGFR-2, CD146, CD130, CD131, stem cell antigen, stem cell factor 1, Tie-2, MCH-H-2Kk and MCH-HLA-DR.

In another embodiment, a bioabsorbable implant is provided, having a tissue contacting surface and a fluid contacting surface, said implant comprising a bioabsorbable, biocompatible first coating for controlled release of one or more pharmaceutical substances from said tissue contacting surface, and a second coating comprising one or more ligands which bind to specific molecules on cell membranes of progenitor endothelial cells on the fluid contacting surface of the medical device. The bioabsorbable implant can be a stent, a vascular or other synthetic graft, or a stent in combination with a synthetic graft. In some embodiments, the tissue contacting surface coating comprises poly(DL-lactide-co-glycolide) and one or more pharmaceutical substances. In other embodiments the tissue contacting surface coating comprises poly(DL-lactide), or poly(lactide-co-glycolide), and paclitaxel.

In one embodiment, the bioabsorbable implant comprises a pharmaceutical substance is at least one of the group consisting of antibiotics/antimicrobials, antiproliferative agents, antineoplastic agents, antioxidants, endothelial cell growth factors, smooth muscle cell growth and/or migration inhibitors, thrombin inhibitors, immunosuppressive agents, anti-platelet aggregation agents, collagen synthesis inhibitors, therapeutic antibodies, nitric oxide donors, antisense oligonucleotides, wound healing agents, therapeutic gene transfer constructs, peptides, proteins, extracellular matrix components, vasodialators, thrombolytics, anti-metabolites, growth factor agonists, antimitotics, steroids, steroidal antiinflammatory agents, chemokines, proliferator-activated receptor-gamma agonists, proliferator-activated receptor-alpha-gamma agonists, proliferator-activated receptor-alpha agonists, proliferator-activated receptor-beta agonists, proliferator-activated receptor-alpha/beta agonists, proliferator-activated receptor-delta agonists, NFκβ, nonsterodial antiinflammatory agents, angiotensin converting enzyme(ACE) inhibitors, free radical scavengers, inhibitors of the CX3CR1 receptor, and anti-cancer chemotherapeutic agents.

In other embodiments, the bioabsorbable implant comprises a pharmaceutical substance selected from the group consisting of cyclosporin A, mycophenolic acid, mycophenolate mofetil acid, rapamycin, rapamycin derivatives, biolimus A9, CCI-779, RAD 001, AP23573, azathioprene, pimecrolimus, tacrolimus (FK506), tranilast, dexamethasone, corticosteroid, everolimus, retinoic acid, vitamin E, rosglitazone, simvastatins, fluvastatin, estrogen, 17β-estradiol, hydrocortisone, acetaminophen, ibuprofen, naproxen, fluticasone, clobetasol, adalimumab, sulindac, dihydroepiandrosterone, testosterone, puerarin, platelet factor 4, basic fibroblast growth factor, fibronectin, butyric acid, butyric acid derivatives, paclitaxel, paclitaxel derivatives, LBM-642, deforolimus, and probucol. In one embodiment, the coating composition can comprise poly(DL-lactide) polymer comprises from about 50 to about 99% of the composition.

In one embodiment, the bioabsorbable implant comprising an outer coating and an inner coating, either or both coatings comprise multiple layers of the poly(DL-lactide) polymer, poly(lactide-co-glycolide) copolymer, or mixture thereof and either or both coatings comprise multiple layers of the pharmaceutical substances.

The invention is also directed to methods of making the biodegradable polymer compositions and methods for making the medical devices from the polymer compositions disclosed herein.

BRIEF DESCRIPTION OF THE DRAWINGS

FIG. 3 is a representative example of a fluorescent micrographs of DAPI stained Kg1a cells bound to bioabsorbable polymer tube with a coating comprising a matrix and anti-CD34 antibodies.

FIG. 4 is a representative example of a fluorescent micrographs of DAPI stained Kg1a cells bound to bioabsorbable polymer tube without a coating or uncoated bioabsorbable polymer tube.

FIG. 5 is a representative example of a fluorescent micrographs of DAPI stained Kg1a cells bound to bioabsorbable polymer tube pre-treated with plasma deposition step.

FIG. 6 is a bar graph which illustrates the data from the various trials from the cell the Kg1a binding experiments using coated and uncoated bioabsorbable polymer tubes.

DETAILED DESCRIPTION

Figure 1:
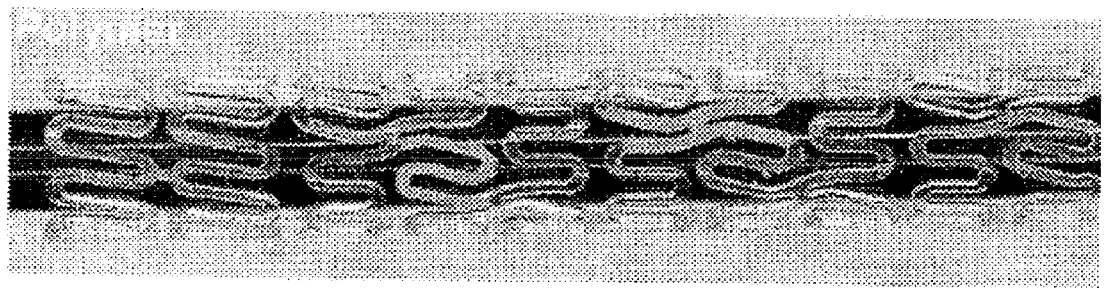
FIG. 1 illustrates an embodiment which consists of a bioabsorbable medical device with a coating.

In embodiments herein there is illustrated bioabsorbable polymeric medical devices having a coating comprising a bioabsorbable, biodegradable polymeric composition for delivering a therapeutic agent, and a ligand for capturing and binding progenitor endothelial cells. Such polymers and medical devices may be more biocompatible and less immunogenic than prior art polymeric medical devices.

In one embodiment, the medical device comprises a crimpable polymeric stent, which can be inserted onto a balloon delivery system for implantation into a tubular organ in the body, for example, into an artery, a duct or vein. Once deployed into an organ, the medical A balloon expandable medical device may comprise a thermal balloon, or non-thermal balloon, and the medical device can have a structure which is crimpable during loading and expandable without stress crazing in physiological conditions.

In another embodiment, the medical device comprises a structure which can orient and/or crystallize upon strain of deployment, for example during balloon dilation, in order to improve its mechanical properties.

In another embodiment, the products resulting from breakdown of the polymers comprising a medical device are "friendly" or less immunogenic to the host, for example to the vascular wall. In yet another embodiment, the medical device comprises polymers having slow breakdown kinetics which avoid tissue overload or other inflammatory responses at the site of implantation. In one embodiment, a medical device may have a minimum of 30-day retention of clinically sufficient strength.

Medical devices of the invention, can be structurally configured to provide the ability to change and conform to the area of implantation to allow for the normal reestablishment of local tissues. The medical devices can transition from solid to a "rubbery state" allowing for easier surgical intervention, than, for example a stainless steel stent.

The polymer composition can comprise a base polymer which can be present from about 60% to 95% by weight, or from about 70% to 80% by weight of the composition. In one embodiment, the polymer formulation can comprise from about 70% by weight poly (L-lactide) (about 1.5 to 3.5 IV or from about 2.5 to 3 IV) with the poly L-lactide-co-TMC (80/20 w/w) (1.0 to 2.6 IV, or from about 1.4 to 1.6 IV).

In another embodiment, the polymer formulation comprises 70% by weight triblock poly L-lactide-co-PEG(95/05 to 99/01, or from 89/2 to 99/01) (2,000 to 10,000 Mw PEG, or from about 6,000 to 8,000 Mw PEG) with the poly L-lactide-co-TMC(70/30) (1.4 to 1.6 IV).

The polymer composition can also comprise a formulation of about 70% by weight diblock poly L-lactide-co-PEG-MME(95/05 to 99/01) (2,000 to 10,000 Mw PEG-MME, or from about 6,000 to 10,000 Mw PEG-MME) with poly L-lactide-co-TMC(70/30 w/w) (1.4 to 1.6 IV).

In one embodiment, pharmaceutical or biological compositions can be incorporated with the polymers by for example grafting to the polymer active sites, or coating. For example, the pharmaceutical or biological compositions may be bound through the end groups of a polymer chain Simple admixing into the polymer or charge-charge interactions may also be employed to associate the pharmaceutical or biological compositions with the polymers.

A medical device of the present invention can comprise any medical device for implantation including stents, grafts, stent grafts, synthetic vascular grafts, shunts, catheters, and the like.

In embodiments disclosed herein, the medical device comprises a stent, which is structurally configured to be deployed into, for example, an artery or a vein, and be able to expand in situ, and conform to the blood vessel lumen to reestablish blood vessel continuity at the site of injury. The stent can be configured to have many different arrangements, and may comprise one or more of the polymeric compositions described herein, so that it is crimpable when loading and expandable and flexible at physiological conditions once deployed.

A biodegradable medical device of the present invention may comprise a base polymer comprising, for example pply L-Lactide or poly D-Lactide, a modifying co-polymer, such as poly L(or D) lactide-co-Tri-methylene-carbonate or poly L(or D)-lactide-co-e-caprolactone as described above.

Various embodiments of biodegradable polymeric stents, and/or stent walls with different configuration are illustrated in FIGS. 1-42. For example, the stent is a tubular structure comprising struts operably designed to allow blood to traverse its walls so that the adjacent tissues are bathed or come in contact with it as blood flows through the area. The particular stent design may depend on the size of the stent radially and longitudinally.

A method of the invention comprises a method for making a bioabsorbable polymeric implant comprising:
  blending a polymer composition comprising a crystallizable composition comprising a base polymer of poly L-lactide or poly D-lactide linked with modifying copolymers comprising poly L(or D)-lactide-co-Tri-methylene-carbonate or poly L(or D)-lactide-co-e-caprolactone in the form of block copolymers or as blocky random copolymers wherein the lactide chain length is sufficiently long enough to allow cross-moiety crystallization;
  molding said polymer composition to structurally configure said implant; and
  cutting said implant to form desired patterns.

A method for fabricating the medical device comprises: preparing a biodegradable polymeric structure; designing said polymeric structure to be configured to allow for implantation into a patient; cutting said structure into patterns configured to permit traversing of the device through openings and to allow for crimping of the device. Of course, the patterns and material comprising the device may be selected to allow for both crimping and expansion.

In another embodiment of the invention, there is provided a medical device for implanting into the lumen of a blood vessel or an organ with a lumen, which device provides a biocompatible system for the delivery of therapeutic agents locally in a safe and controlled manner, and additionally induces the formation of a functional endothelium at the site of injury, which stimulates positive blood vessel remodeling.

One implantable medical device comprises a coating comprising a biocompatible matrix, which can be made of a composition for extended or controlled delivery of a pharmaceutical substance to adjacent tissue. The coating on the medical device further may comprise one or more ligands for capturing target cells on a surface of the medical device (for example, the luminal surface of a stent). Further, the coating may include native/normal or genetically modified target cells which secrete a desired pharmaceutical substance constitutively or when stimulated to do so. In one embodiment, circulating progenitor endothelial cells are the target cells which can be captured and immobilized on the luminal or blood contacting surface of the device to restore, enhance or accelerate the formation of a functional endothelium at the site of implantation of the device due to blood vessel injury.

In one embodiment, the medical device comprises, for example, a stent, a synthetic vascular graft or a catheter having a structure adapted for the introduction into a patient. For example, in the embodiments wherein the medical device is a stent or graft, the device is operably configured to have a luminal or blood contacting surface and an outer surface which is adapted for contacting adjacent tissue when inserted into a patient.

The medical device of the invention can be any device that is implantable into a patient. For example, in one embodiment the device is for insertion into the lumen of a blood vessels or a hollowed organ, such as stents, stent grafts, heart valves, catheters, vascular prosthetic filters, artificial heart, external and internal left ventricular assist devices (LVADs), and synthetic vascular grafts, for the treatment of diseases such as cancer, vascular diseases, including, restenosis, artheroscierosis, thrombosis, blood vessel obstruction, or any other applications additionally covered by these devices.

The medical device of the invention can be any device used for implanting into an organ or body part comprising a lumen, and can be, but is not limited to, a stent, a stent graft, a synthetic vascular graft, a heart valve, a catheter, a vascular prosthetic filter, a pacemaker, a pacemaker lead, a defibrillator, a patent foramen ovale (PFO) septal closure device, a vascular clip, a vascular aneurysm occluder, a hemodialysis graft, a hemodialysis catheter, an atrioventricular shunt, an aortic aneurysm graft device or components, a venous valve, a sensor, a suture, a vascular anastomosis clip, an indwelling venous or arterial catheter, a vascular sheath and a drug delivery port. The medical device can be made of numerous bioabsorbable materials depending on the device, biodegradable materials such as polylactide polymers and polyglycolide polymers or copolymers thereof are the most suitable.

In one embodiment, the medical device comprises a coating comprising a matrix which comprises a nontoxic, biocompatible, bioerodible and biodegradable synthetic material. The coating may further comprise one or more pharmaceutical substances or drug compositions for delivering to the tissues adjacent to the site of implantation, and one or more ligands, such as a peptide, small and/or large molecules, and/or antibodies or combinations thereof for capturing and immobilizing progenitor endothelial cells on the blood contacting surface of the medical device.

In one embodiment, the implantable medical device comprises a stent. The stent can be selected from uncoated stents available in the art. In accordance with one embodiment, the stent is an expandable intraluminal endoprosthesis designed and configured to have a surface for attaching a coating for controlled or slow release of a therapeutic substance to adjacent tissues.

In one embodiment, the controlled-release matrix can comprise one or more polymers and/or oligomers from various types and sources, including, natural or synthetic polymers, which are biocompatible, biodegradable, bioabsorbable and useful for controlled-released of the medicament. For example, in one embodiment, the naturally occurring polymeric materials include proteins such as collagen, fibrin, tropoelastin, elastin, cross-linked tropoelastin and extracellular matrix component, fibrin, fibronectin, laminin, derivatives thereof, or other biologic agents or mixtures thereof. In this embodiment of the invention, the naturally-occurring material can be made by genetic engineering techniques from exogenous genes carried by vectors, such as a plasmid vector and engineered into a host, such as a bacterium. In this embodiment, desired polymer proteins such as tropoelastin and elastin can be produced and isolated for use in the matrix. In alternate embodiments, the naturally occurring polymeric matrices can be purified from natural sources by known methods or they can be obtained by chemical synthesis of the protein polymer. In certain embodiments, the naturally occurring material can be chemically modified or synthesized, for example, by cross-linking the material such as proteins, or by methylation, phosphorylation and the like. In another embodiment, the matrix can comprise a denuded blood vessel or blood vessel scaffolds and/or components thereof.

In one embodiment, the matrix may comprise a synthetic material which include polyesters such as polylactic acid, polyglycolic acid or copolymers and or combinations thereof, a polyanhydride, polycaprolactone, polyhydroxybutyrate valerate, and other biodegradable polymer, or mixtures or copolymers thereof. In this embodiment, the matrix may comprise poly(lactide-coglycolide) as the matrix polymer for coating the medical device. For example, the poly(lactide-co-glycolide) composition may comprise at least one polymer of poly-DL-co-glycolide, poly(D,L-lactide-co-glycolide) or copolymer or mixtures thereof, and it may be mixed together with the pharmaceutical substances to be delivered to the tissues. The coating composition may be applied to the surface of the device using standard techniques such as spraying, dipping, and/or chemical vaporization. Alternatively, the poly (lactide-co-glycolide) (PGLA) solution can be applied as a single layer separating a layer or layers of the pharmaceutical substance(s).

In another embodiment, the coating composition further comprises pharmaceutically acceptable polymers and/or pharmaceutically acceptable carriers, for example, nonabsorbable polymers, such as ethylene vinyl acetate (EVAC) and methylmethacrylate (MMA). The nonabsorbable polymer, for example, can aid in further controlling release of the substance by increasing the molecular weight of the composition thereby delaying or slowing the rate of release of the pharmaceutical substance.

In certain embodiments, the polymer material or mixture of various polymers can be applied together as a composition with the pharmaceutical substance on the surface of the medical device and can comprise a single layer. Multiple layers of composition can be applied to form the coating. In another embodiment, multiple layers of polymer material or mixtures thereof can be applied between layers of the pharmaceutical substance. For example, the layers may be applied sequentially, with the first layer directly in contact with the uncoated surface of the device and a second layer comprising the pharmaceutical substance and having one surface in contact with the first layer and the opposite surface in contact with a third layer of polymer which is in contact with the surrounding tissue. Additional layers of the polymer material and drug composition can be added as required, alternating each component or mixtures of components thereof.

In another embodiment, the matrix may comprise non-polymeric materials such as nanoparticles formed of, for example, metallic alloys or other materials. In this embodiment, the coating on the medical device can be porous and the pharmaceutical substances can be trapped within and between the particles. In this embodiment, the size of the particles can be varied to control the rate of release of the pharmaceutical substance trapped in the particles depending on the need of the patient. In one embodiment, the pharmaceutical composition can be a slow/controlled-release pharmaceutical composition.

Alternatively, the pharmaceutical substance can be applied as multiple layers of a composition and each layer can comprise one or more drugs surrounded by polymer material. In this embodiment, the multiple layers of pharmaceutical substance can comprise a pharmaceutical composition comprising multiple layers of a single drug; one or more drugs in each layer, and/or differing drug compositions in alternating layers applied. In one embodiment, the layers comprising pharmaceutical substance can be separated from one another by a layer of polymer material. In another embodiment, a layer of pharmaceutical composition may be provided to the device for immediate release of the pharmaceutical substance after implantation.

In one embodiment, the pharmaceutical substance or composition may comprise one or more drugs or substances which can inhibit smooth muscle cell migration and proliferation at the site of implantation, can inhibit thrombus formation, can promote endothelial cell growth and differentiation, and/or can inhibit restenosis after implantation of the medical device. Additionally, the capturing of the progenitor endothelial cells on the luminal surface of the medical device may be used to accelerate the formation of a functional endothelium at the site of injury.

Examples of compounds or pharmaceutical compositions which can be incorporated in the matrix, include, but are not limited to prostacyclin, prostacyclin analogs, α-CGRP, α-CGRP analogs or α-CGRP receptor agonists; prazosin; monocyte chemoattactant protein-1 (MCP-1); immunosuppressant drugs such as rapamycin, drugs which inhibit smooth muscle cell migration and/or proliferation, anti-thrombotic drugs such as thrombin inhibitors, immunomodulators such as platelet factor 4 and CXC-chemokine; inhibitors of the CX3CR1 receptor family; antiinflammatory drugs, steroids such as dihydroepiandrosterone (DHEA) testosterone, estrogens such as 17β-estradiol; statins such as simvastatin and fluvastatin; PPAR-alpha ligands such as fenofibrate and other lipid-lowering drugs, PPAR-delta and PPAR-gamma agonists such as rosiglitazone; PPAR-dual-αγ agonists, LBM-642, nuclear factors such as NF-κβ, collagen synthesis inhibitors, vasodilators such as acetylcholine, adenosine, 5-hydroxytryptamine or serotonin, substance P, adrenomedulin, growth factors which induce endothelial cell growth and differentiation such as basic fibroblast growth factor (bFGF), platelet-derived growth factor (PDGF), endothelial cell growth factor (EGF), vascular endothelial cell growth factor (VEGF); protein tyrosine kinase inhibitors such as Midostaurin and imatinib or any anti-angionesis inhibitor compound; peptides or antibodies which inhibit mature leukocyte adhesion, antibiotics/antimicrobials, and other substances such as tachykinins, neurokinins or sialokinins, tachykinin NK receptor agonists; PDGF receptor inhibitors such as MLN-518 and derivatives thereof, butyric acid and butyric acid derivatives puerarin, fibronectin, erythropoietin, darbepotin, serine proteinase-1 (SERP-1) and the like.

In particular embodiments of the invention, one or more of the pharmaceutical substances can be selected from everolimus, rapamycin, pimecrolimus, tacrolimus (FK506), biolimus A9, CCI-779, RAD 001, AP23573, dexamethasone, hydrocortisone, estradiol, acetaminophen, ibuprofen, naproxen, fluticasone, clobetasol, adalimumab, sulindac, and combinations thereof. The aforementioned compounds and pharmaceutical substances can be applied to the coating on the device alone or in combinations and/or mixtures thereof.

In one embodiment, the implantable medical device can comprise a coating comprising one or more barrier layers in between said one or more layers of matrix comprising said pharmaceutical substances. In this embodiment, the barrier layer may comprise a suitable biodegradable material, including but not limited to suitable biodegradable polymers including: polyesters such as PLA, PGA, PLGA, PPF, PCL, PCC, TMC and any copolymer of these; polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L-lactide), poly(lactic acid-co-glycolic acid), 50/50 (DL-lactide-co-glycolide); polydixanone; polypropylene fumarate; polydepsipeptides; polycaprolactone and co-polymers and mixtures thereof such as poly(D, L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate. Of course, such materials may in fabrication of the medical device be disposed in an appropriate solvent, such as water, ethanol, acetone etc. and may include materials providing for radioopacity, such as diatrizoate sodium, tantalum etc. The number of barrier layers that the coating on a device may have depends on the amount of therapeutic needed as dictated by the therapy required by the patient. For example, the longer the treatment, the more therapeutic substance required over a period of time, the more barrier layers may be needed to provide the pharmaceutical substance in a timely and continued manner.

In one embodiment, the ligand is applied to the blood contacting surface of the medical device and the ligand specifically recognizes and binds a desired component or epitope on the surface of target cells in the circulating blood. In one embodiment, the ligand is specifically designed to recognize and bind only the genetically-altered mammalian cell by recognizing only the genetically-engineered marker molecule on the cell membrane of the genetically-altered cells. The binding of the target cells immobilizes the cells on the surface of the device.

In an alternate embodiment, the ligand on the surface of the medical device for binding the genetically-altered cell is selected depending on the genetically engineered cell membrane marker molecule. That is, the ligand binds only to the cell membrane marker molecule or antigen which is expressed by the cell from extrachromosamal genetic material provided to the cell so that only the genetically-modified cells can be recognized by the ligand on the surface of the medical device. In this manner, only the genetically-modified cells can bind to the surface of the medical device. For example, if the mammalian cell is an endothelial cell, the ligand can be at least one type of antibody, antibody fragments or combinations thereof the antibody may be specifically raised against a specific target epitope or marker molecule on the surface of the target cell. In this aspect of the invention, the antibody can be a monoclonal antibody, a polyclonal antibody, a chimeric antibody, or a humanized antibody which recognizes and binds only to the genetically-altered endothelial cell by interacting with the surface marker molecule and, thereby modulating the adherence of the cells onto the surface of the medical device. The antibody or antibody fragment of the invention can be covalently or noncovalently attached to the surface of the matrix, or tethered covalently by a linker molecule to the outermost layer of the matrix coating the medical device. In this embodiment, for example, the monoclonal antibodies can further comprises Fab or F(ab')2 fragments. The antibody fragment of the invention comprises any fragment size, such as large and small molecules which retain the characteristic to recognize and bind the target antigen as the antibody.

In another embodiment, the antibody or antibody fragment of the invention recognize and bind antigens with specificity for the mammal being treated and their specificity is not dependent on cell lineage. In one embodiment, for example, in treating restenosis wherein the cells may not be genetically modified to contain specific cell membrane marker molecules, the antibody or fragment is specific for selecting and binding circulating progenitor endothelial cell surface antigen such as CD133, CD34, CD14, CDw90, CD117, HLA-DR, VEGFR-1, VEGFR-2, Muc-18 (CD146), CD130, stem cell antigen (Sca-1), stem cell factor 1 (SCF/c-Kit ligand), Tie-2, MHC such as H-2Kk and HLA-DR antigen.

In another embodiment, the coating of the medical device comprises at least one layer of a biocompatible matrix as described above, the matrix comprises an outer surface for attaching a therapeutically effective amount of at least one type of small molecule of natural or synthetic origin. The small molecule recognizes and interacts with, for example, progenitor endothelial cells in the prevention, amelioration or treatment of restenosis, to immobilize the cells on the surface of the device to form an endothelial layer. The small molecules can be used in conjunction with the medical device for the treatment of various diseases, and can be derived from a variety of sources such as cellular components such as fatty acids, proteins, nucleic acids, saccharides and the like, and can interact with an antigen on the surface of a progenitor endothelial cell with the same results or effects as an antibody. In one aspect of this embodiment, the coating on the medical device can further comprise a compound such as a growth factor as described herewith in conjunction with the coating comprising an antibody or antibody fragment.

In another embodiment, the coating of the medical device comprises at least one layer of a biocompatible matrix as described above, the matrix comprising a luminal surface for attaching a therapeutically effective amount of at least one type of small molecule of natural or synthetic origin. The small molecule recognizes and interacts with an antigen on the target cell such as a progenitor endothelial cell surface to immobilize the progenitor endothelial cell on the surface of the device to form endothelium. The small molecules can be derived from a variety of sources such as cellular components including, fatty acids, peptides, proteins, nucleic acids, saccharides and the like and can interact, for example, with a structure such as an antigen on the surface of a progenitor endothelial cell with the same results or effects as an antibody.

In another embodiment, there is provided a method for treating, ameloriating, or preventing vascular disease such as restenosis and artherosclerosis, comprising administering a pharmaceutical substance locally to a patient in need of such substance. The method comprises implanting into a vessel or hollowed organ of a patient a medical device with a coating, which coating comprises a pharmaceutical composition comprising a drug or substance for inhibiting smooth muscle cell migration and thereby restenosis, and a biocompatible, biodegradable, bioerodible, nontoxic polymer or non-polymer matrix, wherein the pharmaceutical composition comprises a slow or controlled-release formulation for the delayed release of the drug. The coating on the medical device can also comprise a ligand such as an antibody for capturing cells such as endothelial cells and or progenitor cells on the luminal surface of the device so that a functional endothelium is formed.

In another embodiment, there is provided a method of making a coated medical device or a medical device with a coating, which comprises applying to a surface of a medical device a polymer or non-polymer matrix and a pharmaceutical composition comprising one or more drugs, and applying a ligand to the medical device so that the ligand attaches to a surface of the device and is designed to bind molecules on the cell membrane of circulating native or genetically engineered cells. In this embodiment, the polymer matrix comprises a biocompatible, biodegradable, nontoxic polymer matrix such as collagen, tropocollagen, elastin, tropoelastin, cross-linked tropoelastin, poly(lactide-co-glycolide) copolymer, polysaccharides and one or more pharmaceutical substances, wherein the matrix and the substance(s) can be mixed prior to applying to the medical device. In this embodiment, at least one type of ligand is applied to the surface of the device and can be added on top or on the outer surface of the device with the drug/matrix composition in contact with the device surface. The method may alternatively comprise the step of applying at least one layer of a pharmaceutical composition comprising one or more drugs and pharmaceutically acceptable carriers, and applying at least one layer of a polymer matrix to the medical device.

In one embodiment, the matrix can be applied as one or more layers and with or without the pharmaceutical substance, and the ligand can be applied independently to the medical device by several methods using standard techniques, such as dipping, spraying or vapor deposition. In an alternate embodiment, the polymer matrix can be applied to the device with or without the pharmaceutical substance. In this aspect of the invention wherein a polymer matrix is applied without the drug, the drug can be applied as a layer between layers of matrices. In other embodiments, a barrier layer is applied between the layers comprising the pharmaceutical substances.

In one embodiment, the method comprises applying the pharmaceutical composition as multiple layers with the ligand applied on the outermost surface of the medical device so that the ligand such as antibodies can be attached in the luminal surface of the device. In one embodiment, the method for coating the medical device comprises: applying to a surface of said medical device at least one or more layers of a matrix, one or more pharmaceutical substance(s), and a basement membrane component; applying to said at least one layer of said composition on said medical device a solution comprising at least one type of ligand for binding and immobilizing genetically-modified target cells; and drying said coating on the medical device, such as a stent, under vacuum at low temperatures.

In another embodiment, the coating is comprised of a multiple component pharmaceutical composition within the matrix such as containing a fast release pharmaceutical agent to retard early neointimal hyperplasia/smooth muscle cell migration and proliferation, and a secondary biostable matrix that releases a long acting agent for maintaining vessel patency or a positive blood vessel remodeling agent, such as endothelial nitric oxide synthase (eNOS), nitric oxide donors and derivatives such as aspirin or derivatives thereof, nitric oxide producing hydrogels, PPAR agonist such as PPAR-A ligands, tissue plasminogen activator, statins such as atorvastatin, erythropoietin, darbepotin, serine proteinase-1 (SERP-1) and pravastatin, steroids, and/or antibiotics.

In another embodiment, there is provided a therapeutic, drug delivery system and method for treating diseases in a patient. The therapeutic or drug delivery system comprises a medical device with a coating composed of a matrix comprising at least one type of ligand for recognizing and binding target cells such as progenitor endothelial cells or genetically-altered mammalian cells and genetically-altered mammalian cells which have been at least singly or dually-transfected.

In one embodiment, the coating on the present medical device comprises a biocompatible matrix and at least one type of pharmaceutical substance or ligand, which specifically recognizes and bind target cells such as progenitor endothelial cells such as in the prevention or treatment of restenosis, or genetically-altered mammalian cells, onto the surface of the device, such as in the treatment of blood vessel remodeling and cancer.

Additionally, the coating of the medical device may optionally comprise at least an activating compound for regulating the expression and secretion of the engineered genes of the genetically-altered cells. Examples of activator stimulatory compounds, include but is not limited to chemical moieties, and peptides, such as growth factors. In embodiments when the coating comprises at least one compound, the stimulus, activator molecule or compound may function to stimulate the cells to express and/or secrete at least one therapeutic substance for the treatment of disease.

In one embodiment, the coating on the medical device comprises a biocompatible matrix which comprises an outer surface for attaching a therapeutically effective amount of at least one type of ligand such as an antibody, antibody fragment, or a combination of the antibody and the antibody fragment, or at least one type of molecule for binding the engineered marker on the surface of the genetically-modified cell. The antibody or antibody fragment present recognizes and binds an antigen or the specific genetically-engineered cell surface marker on the cell membrane or surface of target cells so that the cells are immobilized on the surface of the device. In one embodiment, the coating may optionally comprise an effective amount of at least one compound for stimulating the immobilized progenitor endothelial cells to either accelerate the formation of a mature, functional endothelium if the target cells are circulating progenitor cells, or to stimulate the bound cells to express and secrete the desired gene products if the target are genetically-altered cells on the surface of the medical device.

In one embodiment, the compound of the coating of the invention, for example in treating restenosis, comprises any compound which stimulates or accelerates the growth and differentiation of the progenitor cell into mature, functional endothelial cells. In another embodiment, the compound is for stimulating the genetically modified cells to express and secrete the desired gene product. For example, a compound for use in the invention may be a growth factor such as vascular endothelial growth factor (VEGF), basic fibroblast growth factor, platelet-induced growth factor, transforming growth factor beta 1, acidic fibroblast growth factor, osteonectin, angiopoietin 1 (Ang-1), angiopoietin 2 (Ang-2), insulin-like growth factor, granulocyte-macrophage colony-stimulating factor, platelet-derived growth factor AA, platelet-derived growth factor BB, platelet-derived growth factor AB and endothelial PAS protein 1.

In another embodiment, for example when using genetically-altered mammalian cells, the activating agents or compounds useful for stimulating the cells to express and secrete the genetically-engineered gene products include, but are not limited to estrogen, tetracycline and other antibiotics, tamoxiphen, etc., and can be provided to the patient via various routes of administration, such as through the skin via a patch and subcutaneously.

The invention also provides methods for treating, ameliorating, and preventing a variety of diseases, such as vascular disease, cancer, blood vessel remodeling, severe coronary artery disease artherosclerosis, restenosis, thrombosis, aneurysm and blood vessel obstruction. In one embodiment, there is provided a method for retaining or sealing the medical device insert to the vessel wall, such as a stent or synthetic vascular graft, heart valve, abdominal aortic aneurysm devices and components thereof, and for establishing vascular homeostasis, thereby preventing excessive intimal hyperplasia as in restenosis. In a method of treating atherosclerosis, the artery may be either a coronary artery or a peripheral artery such as the femoral artery. Veins can also be treated using these techniques and medical device.

With respect to the treatment, amelioration, and prevention of restenosis, the invention also provides an engineered method for inducing a healing response. In one embodiment, a method is provided for rapidly inducing the formation of a confluent layer of endothelium in the luminal surface of an implanted device in a target lesion of an implanted vessel, in which the endothelial cells express nitric oxide synthase and other anti-inflammatory and inflammation-modulating factors. The invention also provides a medical device which has increased biocompatibility over prior art devices, and decreases or inhibits tissue-based excessive intimal hyperplasia and restenosis by decreasing or inhibiting smooth muscle cell migration, smooth muscle cell differentiation, and collagen deposition along the inner luminal surface at the site of implantation of the medical device.

In an embodiment, a method for coating a medical device comprises the steps of: applying at least one layer of a biocompatible matrix to the surface of the medical device, wherein the biocompatible matrix comprises at least one component selected from the group consisting of a polyurethane, a segmented polyurethane-urea/heparin, a poly-L-lactic acid, a cellulose ester, a polyethylene glycol, a polyvinyl acetate, a dextran, gelatin, collagen, elastin, tropoelastin, laminin, fibronectin, vitronectin, heparin, fibrin, cellulose and carbon and fullerene, and applying to the biocompatible matrix, simultaneously or sequentially, a therapeutically effective amounts of at least one type of antibody, antibody fragment or a combination thereof, and at least one compound which stimulates endothelial cell growth and differentiation.

A bioabsorbable, biocompatible, and biodegradable scaffold may be operatively configured to afford deliverability, flexibility, and radial stretchability very suitable for implantation in the pulsatile movements, contractions and relaxations of, for example, the cardiovascular system.

For example, the medical device could comprise a polymer with low immune rejection properties such as a bioabsorbable polymer composition or blend, having a combination of mechanical properties balancing elasticity, rigidity and flexibility. The polymer composition could produce a low antigenicity by means of a biocompatible base material, such as, without limitation, a bioabsorbable polymer, copolymer, or terpolymer, and a copolymer or terpolymer additive. These kinds of polymer structures may advantageously undergo enzymatic degradation and absorption within the body. In particular, the novel composition may allow for a "soft" breakdown mechanism that is so gradual that the breakdown products or polymer components are less injurious to the surrounding tissue and thus reduce restenotic reactions or inhibit restenosis entirely.

The present inventors have also proposed novel designs which may employ such bioabsorbable, biocompatible and biodegradable material to make advantageous scaffolds, which may afford a flexibility and stretchability very suitable for implantation in the pulsatile movements, contractions and relaxations of, for example, the cardiovascular system.

Embodiments disclosed herein include, medical devices such as stents, deformable vascular devices, synthetic grafts and catheters, which may or may not comprise a bioabsorbable polymer composition for implantation into a patient.

In one embodiment, a cardiovascular tube-shaped expandable scaffold such as a stent is provided, having a low rejection or immunogenic effect after implantation, which is fabricated from a bioabsorbable polymer composition or blend having a combination of mechanical properties balancing vascular scaffolding, elasticity, rigidity and flexibility, which properties allow bending and crimping of the scaffold tube onto an expandable delivery system for vascular implantation. The instant devices can be used in the treatment of, for example, vascular disease such as atherosclerosis, restenosis, and vascular remodeling provided as both a crimped and expanded structure, which can be used in conjunction with balloon angioplasty.

In an embodiment, the medical device can be provided as an expandable scaffold, comprising a plurality of meandering strut elements or structures forming a consistent pattern, such as ring-like structures along the circumference of the device in repeat patterns (e.g., with respect to a stent, without limitation, throughout the structure, at the open ends only, or a combination thereof). The meandering strut structures can be positioned adjacent to one another and/or in oppositional direction allowing them to expand radically and uniformly throughout the length of the expandable scaffold along a longitudinal axis of the device. In one embodiment, the expandable scaffold can comprise specific patterns such as a lattice structure, dual-helix structures with uniform scaffolding with optional side branching.

An embodiment provides an expandable biodegradable tubular scaffold which includes a plurality of biodegradable first meanders forming an interconnected mesh, wherein the mesh extends circumferentially about a longitudinal axis; wherein each of the biodegradable first meanders are manufactured from a polymer which crystallizes under the strain of expansion of said tubular scaffold, and a plurality of biodegradable second meanders, each of said second meanders being separate from another, and each extending circumferentially about said longitudinal axis in a single orthogonal plane. The second meanders nest in, and interconnect to, the first meanders, and have at least two closed loop connectors intervening between segments of each second meanders, which connectors are capable of deformation and crystallization under full expansion during intravascular implantation of said tubular scaffold. This extra expansion range serves to prevent overstretching the second meanders or hoops and thereby necking or structural integrity of the second meanders or hoops.

In one embodiment, a bioabsorbable and flexible scaffold circumferential about a longitudinal axis so as to form a tube, the tube having a proximal open end and a distal open end, and being expandable from an unexpanded structure to an expanded form, and being crimpable, the scaffold having a patterned shape in expanded form comprising:

a plurality of first meandering strut patterns, each of the first meandering strut pattern being interconnected to one another to form an interconnected mesh pattern circumferential about the longitudinal axis;

at least two second strut patterns nested within the interconnected mesh pattern, each of said second strut patterns comprising a hoop circumferential about the longitudinal axis, said hoop having an inner surface proximal to the longitudinal axis and an outer surface distal to the longitudinal axis, the hoop inner and outer surfaces about their circumferences being orthogonal to the longitudinal axis and within substantially the same plane; and at least two expansion loops intervening in the second meanders so as provide extra hoop length when stretched to the crystallized limit at which the second meanders would neck and fail.

In one embodiment, the first meandering strut patterns can be generally parallel to said longitudinal axis, generally diagonal to said longitudinal axis, generally orthogonal to said longitudinal axis, or generally concentric about said longitudinal axis. The second strut patterns can be made of a material which substantially crystallizes when said tube is in its expanded state, but does not substantially crystallize in its unexpanded state. The second strut patterns can include at least one hoop having a through-void, wherein said at least one hoop is configured to permit its radius to be expanded when said at least one hoop is subject to an expanding force which exceeds its nominal expanded state, but a force that does not result in hoop failure.

In one embodiment, each of the first meandering strut patterns of the scaffold is essentially sinusoidal, and each of the second strut patterns is substantially non-sinusoidal. The first meandering strut patterns of a scaffold can extend from the proximal open end to the distal open end of the tube. in another embodiment, each of the second strut patterns can be found at the proximal open end and the distal open end. In one embodiment, each of the second strut patterns is further found between the proximal open end and the distal open end.

In one embodiment, the scaffold comprises a structure wherein each of the second strut patterns can be found between the proximal open end and the distal open end but not at the proximal open end or distal open end. In another embodiment, the scaffold comprises a structure wherein the second strut patterns can be found at least one of the proximal open end or the distal open end.

In a specific embodiment, the scaffold comprises a stent having an unexpanded configuration and an expanded configuration; an outer tubular surface and an inner tubular surface, the stent comprising: a plurality of biodegradable, paired, separate circumferential bands having a pattern of distinct undulations in an unexpanded configuration and substantially no undulations in an expanded configuration, the undulations of the biodegradable, paired, separate circumferential bands in the stent in an unexpanded state being incorporated into a substantially planar ring in an expanded state, and a plurality of biodegradable interconnection structures spanning between each pair of circumferential bands and connected to multiple points on each band of the paired bands.

In an embodiment, the stent interconnecting structures comprise a pattern of undulations both in an unexpanded and expanded configuration. In an alternate embodiment, the interconnection structures comprise a pattern containing no undulations in both an unexpanded and expanded configuration. The interconnection structures of the stent can expand between undulations of paired circumferential bands.

In another embodiment, a biosorbable and flexible scaffold circumferential about a longitudinal axis and substantially forming a tube, the tube having a proximal open end and a distal open end, and being crimpable and expandable, and comprising in expanded form: a) at least two rings circumferential about the longitudinal axis, the rings having an inner surface proximal to the longitudinal axis, an outer surface distal to the longitudinal axis, a top surface proximal to the proximal open end and a bottom surface proximal to the distal open end, the ring inner and outer surfaces about their circumferences being orthogonal to the longitudinal axis and within substantially the same plane, and b) a plurality of meandering strut patterns located between the at least two rings and circumferential coursing about the longitudinal axis; the plurality of meandering strut patterns connected to the rings at least two connection points on the circumference of each ring, and each connection point on the circumference of the ring on both the top ring surface and the bottom ring surface; wherein each of the connection points with any particular ring is symmetrical in structure above and below the upper and lower surface of the ring.

In one embodiment, the scaffold comprises a structure wherein the connection points of the rings, the meandering strut patterns above the ring upper surface and below the ring lower surface in conjunction form a stylized, letter H configuration. In another embodiment, the scaffold can comprise a structure wherein at the connection points of the rings, the meandering strut patterns above the ring upper surface and below the ring lower surface in conjunction form two abutting sinusoids. In an alternate embodiment, the scaffold can comprise a structure wherein at the connection points of the rings, the meandering strut patterns above the ring upper surface and below the ring lower surface in conjunction form two sinusoids with intervening structure connecting the same and the ring. In one embodiment, the connection points of the rings have between 2 through 6 meandering strut pattern connections at each connection.

In another embodiment, an expandable biodegradable tubular scaffold comprising a plurality of biodegradable first meanders forming an interconnected mesh. The mesh extending circumferentially about a longitudinal axis; wherein each of the biodegradable first meanders are manufactured from a racemic polymer which crystallizes under the strain of expansion of the tubular scaffold, and also comprising a plurality of biodegradable second meanders, each of the second meanders being separate from another, and each extending circumferentially about the longitudinal axis in a single plane, the second meanders being nested in, and interconnected to, the first meanders. In this embodiment, the scaffold's first meanders are generally parallel to the longitudinal axis, generally diagonal to the longitudinal axis, generally orthogonal to the longitudinal axis, or are concentric about the longitudinal axis. The second meanders are made from a material which crystallizes when the tube is in its expanded state, but does not substantially crystallize in its unexpanded state, and at least one of the second meanders includes at least one through-void, which is configured to permit stretching of the second member without failure of the member.

In one embodiment, the first meanders form a strut pattern that is sinusoidal when the tube is in an expanded form, the second meanders form a strut pattern that is substantially non-sinusoidal when the tube is in an expanded form. In this and other embodiments, the first meanders form a strut pattern that extends from the proximal open end to the distal open end of the tube, and the second meanders form a strut pattern that is found at the proximal open end and the distal open end. The second meanders can also form a strut pattern that is further found between the proximal open end and the distal open end, or the second meanders form a pattern that is found between the proximal open end and the distal open end but not at the proximal open end or the distal open end.

In another embodiment, the stent conformation is variably adaptable to luminal diameters of the cardiovascular contours such that the second meander can be flexibly expanded beyond the rigidly and elastically stretched stable hoop conformation beyond the maximal crystallization stage, however, without causing collapse of the hoop structure. This additional built-in flexible expansion is obtained by the special loop inserts along the second meander struts. More specifically, such a loop interconnects at least two segments of the second meander strut, wherein the loop before expansion forms an oval ring lying in a longitudinal axis direction. When the second meander at its maximal stretch expansion to form a hoop structure has to be further expanded for a better luminal fit or hold in the vascular system in situ, the loop can be stretched orthogonally forming an oval ring in the direction of the stretched hoop structure.

In one embodiment, at least one of the plurality of paired biodegradable circumferential bands includes along its outer tubular surface, a radio-opaque material capable of being detectable by radiography, MRI or spiral CT technology. Alternatively, at least one of the interconnection structures includes a radio-opaque material along its outer tubular surface, which can be detectable by radiography, MRI or spiral CT technology. The radio-opaque material can be housed in a recess on one of the circumferential bands, or in a recess on one of the interconnection structures. In one embodiment, a least one of the interconnection structures and at least one of the circumferential bands includes a radio-opaque material along the outer tubular surface, which is detectable by radiography, MRI or spiral CT technology.

In an alternate embodiment, a method for fabricating a tube-shaped scaffold comprises: preparing a racemic poly-lactide mixture; fabricating a biodegradable polymer tube of the racemic poly-lactide mixture; laser cutting the tube until a desired scaffold is formed. In one option of such embodiment, the fabrication of the scaffold can be performed using a molding technique, which is substantially solvent-free, or an extrusion technique.

There is also provided a method for fabricating the tube-shaped scaffold comprising, blending a polymer composition comprising a crystallizable composition comprising a base polymer of poly L-lactide or poly D-lactide linked with modifying copolymers comprising poly L(or D)-lactide-co-trimethylene-carbonate or poly L(or D)-lactide-co-ε-caprolactone in the form of block copolymers or as blocky random copolymers wherein the lactide chain length is sufficiently long enough to allow cross-moiety crystallization; molding the polymer composition to structurally configure the scaffold; and cutting the scaffold to form the desired scaffold patterns. In this embodiment. the blended composition may comprise a racemic mixture of poly L-lactide and poly-D lactide. Accordingly, medical devices such as a stent, produced by this method may consist essentially of a racemic mixture of a poly-L and poly-D lactide. In this embodiment, the stent can comprise other polymer materials such as trimethylcarbonate. In one optional composition of such embodiment wherein the device comprises trimethylcarbonate, the amount of trimethylcarbonate does not exceed more than 40% of the weight of the stent.

In another embodiment, an expandable tube-shaped scaffold having a proximal end and a distal end defined about longitudinal axis is provided. The scaffold comprises: (a) a plurality of first meandering strut elements interconnected with one another at least one point in such a manner to form a circumferential tube-shaped structure, the first meandering strut elements forming a tubular mesh which is crimpable and expandable; (b) a second meandering strut element which is operatively configured to be crimpable and expandable and configured to form a hoop-shaped strut of the scaffold after expansion; and (c) a locking means permitting the scaffold to the locked in a crimped position; wherein the scaffold comprises a expansion crystallizable, bioabsorbable racemate polymer composition or blend.

In one lock embodiment, the tube-shaped scaffold can comprise a structure wherein the locking means is a two-part portion of one or different meandering strut elements located at or near both the proximal and distal ends of the tube-shaped scaffold. In this embodiment, the two-part portion of the locking means can entail, for example, a snap-fit engagement in the crimped position of the scaffold, wherein the locking means is disengaged by scaffold expansion. In alternate embodiments, the tube-shaped scaffold can comprise a locking means comprising a snap-fit key-in-lock configuration wherein the design resembles a dovetail type interlocking means. The tube-shaped scaffold can also comprise locking means comprising a snap-fit key-in-lock configuration resembling a ball-joint type interlocking means; a cantilever arm hooking an oppositely shaped end piece of the plastic scaffold, and the like.

The tube-shaped scaffold can be mounted or carried on a expandable balloon carrier device and can be sized to stretch from a crimped tube diameter to a diameter sufficient for implantation inside the lumen of a vascular system.

In another embodiment, the expandable scaffold comprises a set of interlocking meandering struts stabilizing the implanted scaffold in an expanded or implanted configuration, wherein the scaffold polymer undergoes a molecular reorientation and crystallization during the radial strain of expansion. The scaffold can vary from a cylindrical to a conal shape or combination thereof. In the embodiments described herein, the scaffold's biodegradable polymer displays breakdown kinetics sufficiently slow to avoid tissue overload or other inflammatory reactions. The polymer core material comprising at least one encapsulated drug for localized treatment of the vascular wall and lumen.

In certain embodiments, novel stent designs with coatings are provided which are bioabsorbable, biocompatible, and biodegradable. Scaffolds made from such material may afford deliverability, flexibility, and radial stretchability very suitable for implantation in the pulsatile movements, contractions and relaxations of, for example, the cardiovascular system. After a period of implantation, the stent may begin to degrade once normal endothelium has been established by the presence of the coating.

For example, the medical device could comprise a polymer with low immune rejection properties such as a bioabsorbable polymer composition or blend, having a combination of mechanical properties balancing elasticity, rigidity and flexibility. The polymer composition could produce a low antigenicity by means of a biocompatible base material, such as, without limitation, a bioabsorbable polymer, copolymer, or terpolymer, and a copolymer or terpolymer additive. These kinds of polymer structures may advantageously undergo enzymatic degradation and absorption within the body. In particular, the novel composition may allow for a "soft" breakdown mechanism that is so gradual that the breakdown products or polymer components are less injurious to the surrounding tissue and thus reduce restenotic reactions or inhibit restenosis entirely.

In certain embodiments, there are provided polymeric designs, with coatings which may employ bioabsorbable, biocompatible and biodegradable material to make advantageous scaffolds, which may afford flexibility and stretchability very suitable for implantation in the pulsatile movements, contractions and relaxations of, for example, the cardiovascular system. In these embodiments, the coatings can be applied prior to or cutting or making the designs. The coatings can be applied in various manners, and can vary in content depending on the site of application on the device. For example, a coating on a luminal surface of the medical device can comprise ligands for recognizing and binding endothelial cells to form an endothelium, and can also comprise one or more pharmaceutical substances for inducing differentiation of endothelial cells and/or maintaining the endothelial cells function. In this and other embodiments, the abluminal coating can comprise one or more pharmaceutical substances for example, that inhibit restenosis or prevent thrombus formation.

The coating can comprise one or more layers of a matrix and at least one type of ligand such as antibodies, antibody fragments or combinations or antibodies and antibody fragments; peptides and small molecules which bind and capture endothelial cells in vivo at the site of implantation of the device. The coating can further comprise a pharmaceutical substance for delivery to target tissue. In this embodiment, pharmaceutical substances, for example, for reducing restenosis, inhibit smooth muscle cell migration, induce nitric oxide synthetase, can be used in conjuction with the coating. The pharmaceutical substances can be applied in various manner such as in layers.

FIG. 1 is a photograph of a bioabsorbable medical device of the invention consisting of a stent design mounted along its longitudinal axis on a catheter. In this embodiment, the stent is coated with matrix layer comprising a bioabsorbable polymer and a ligand consisting of antibodies against CD34 positive cells.

The figures provided herewith depict embodiments that are described as illustrative examples that are not deemed in any way as limiting the present invention.

EXAMPLE 1

Bioabsorbable polymer tubes for use to make an embodiment of the invention were made from polymer compositions as described above. Uncoated tubes and tubes that had been coated as described above, comprising a coating with Anti-CD34 antibodies coated on a polymer matrix were analyzed for the ability to bind antibodies on their surface. Prior to testing the tubes for cell binding, tubes that were coated with a layer of antibodies were examined for the amount of antibody binding on their surface. The experiments were repeated three times. The results of these studies are shown in FIG. 2.

Figure 2:
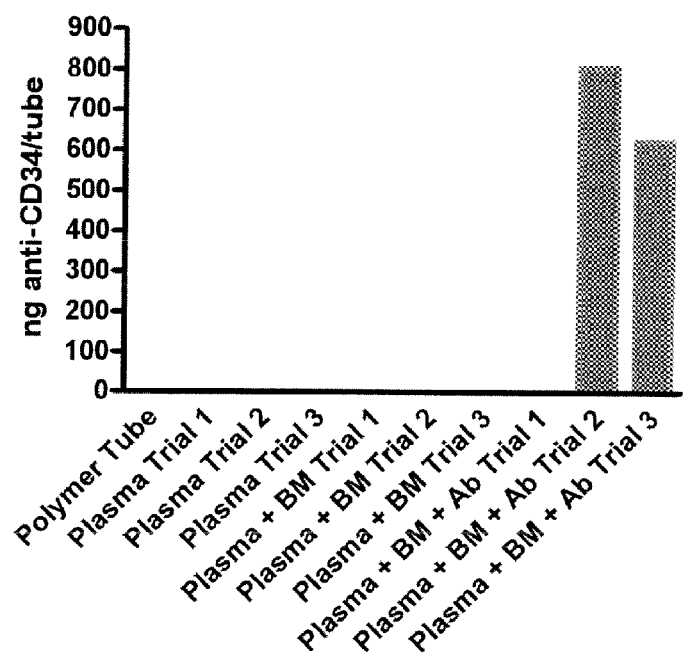
FIG. 2 depicts representative data from experiments wherein the amount of anti-CD34 antibody was measured on bioabsorbable polymeric tubes.

As seen in FIG. 2, the untreated tube, plasma treated with an oxygen plasma followed by an argon plasma tubes, and tubes coated with a matrix did not contain any anti-CD34 antibodies per tube in any of the trials performed. In contrast polymer tube were coated with a coating solution comprising a bioabsorbable polymer, followed by a buffered solution containing anti-CD34 antibodies had approximately 600 to 800 ng of antibodies (per tube) attached to their surface. The tubes were then tested for cell binding activity in in vitro experiments using Kg1a, CD34 positive cells. Only those tubes processed to be coated with solutions containing anti-CD34 were found to contain bound antibody on their surface.

EXAMPLE 2

The uncoated and coated tubes and tubes that were plasma treated were incubated with Kg1a cells. After incubation, the tubes were rinsed in buffered saline to remove unbound cells and the tubes were fixed and process to identify cells bound to the devices. Cell binding to the tubes was determined by staining the tubes tested after incubation with a fluorescent, nuclear, DAPI ((4',6-diamidino-2-phenylindole)dihydrochloride) staining procedure and examined under a fluorescent microscope. The results of these experiments are shown in FIGS. 3 through 6.

Figure 7A:
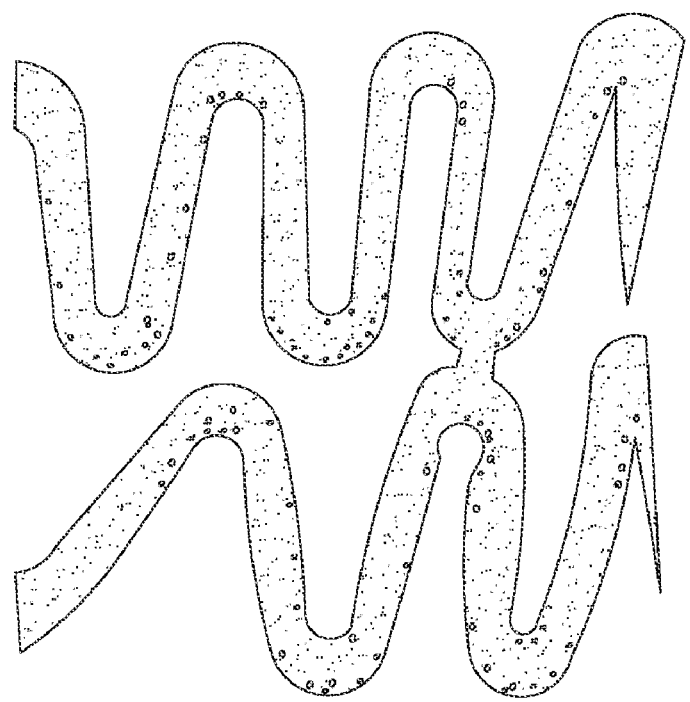
FIG. 7A is a representative example of a fluorescent micrographs of DAPI stained Kg1a cells bound to bioabsorbable polymer stent of the invention.
Figure 7B:
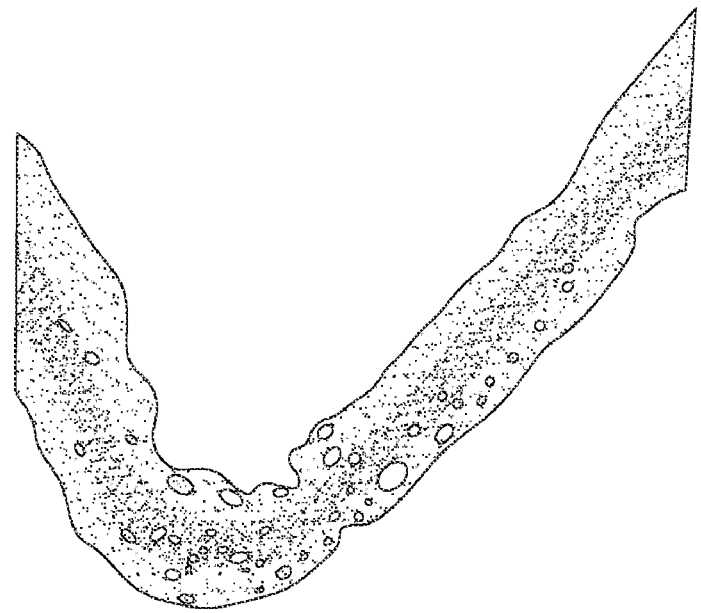
FIG. 7B is a representative example of a fluorescent micrographs of DAPI stained Kg1a cells bound to a bioabsorbable polymer stent strut shown in FIG. 7A, seen here at a higher magnification.

FIG. 3 shows a representative bioabsorbable tube with a coating comprising a polymer and anti-CD34 antibodies which depicts numerous Kg1a cells attached to the tube as seen by the fluorescence emitted from the cells. FIG. 4 is a representative uncoated tube from the experiments and shows that the uncoated tubes had very few cells attached thereon. It appeared that the majority of the signal from these groups was due to background fluorescence. FIG. 5 is a representative of the plasma treated tubes which shows that binding of cells also occurred in tubes, but the binding was confined to one end of the tube. The data for these experiments is summarized in FIG. 6. FIG. 6 is a table showing that having a matrix and antibody coating on the bioabsorbable device enhances the binding of cells to device. Similar experiments were carried out using bioabsorbable stents made by the present methods. An exemplary bioabsorbable stent with a coating comprising a polymer and anti-CD34 antibodies which was exposed to Kg1a cells as discussed above shows that Kg1a bound to its surface as seen in FIG. 7.

Figure 8:
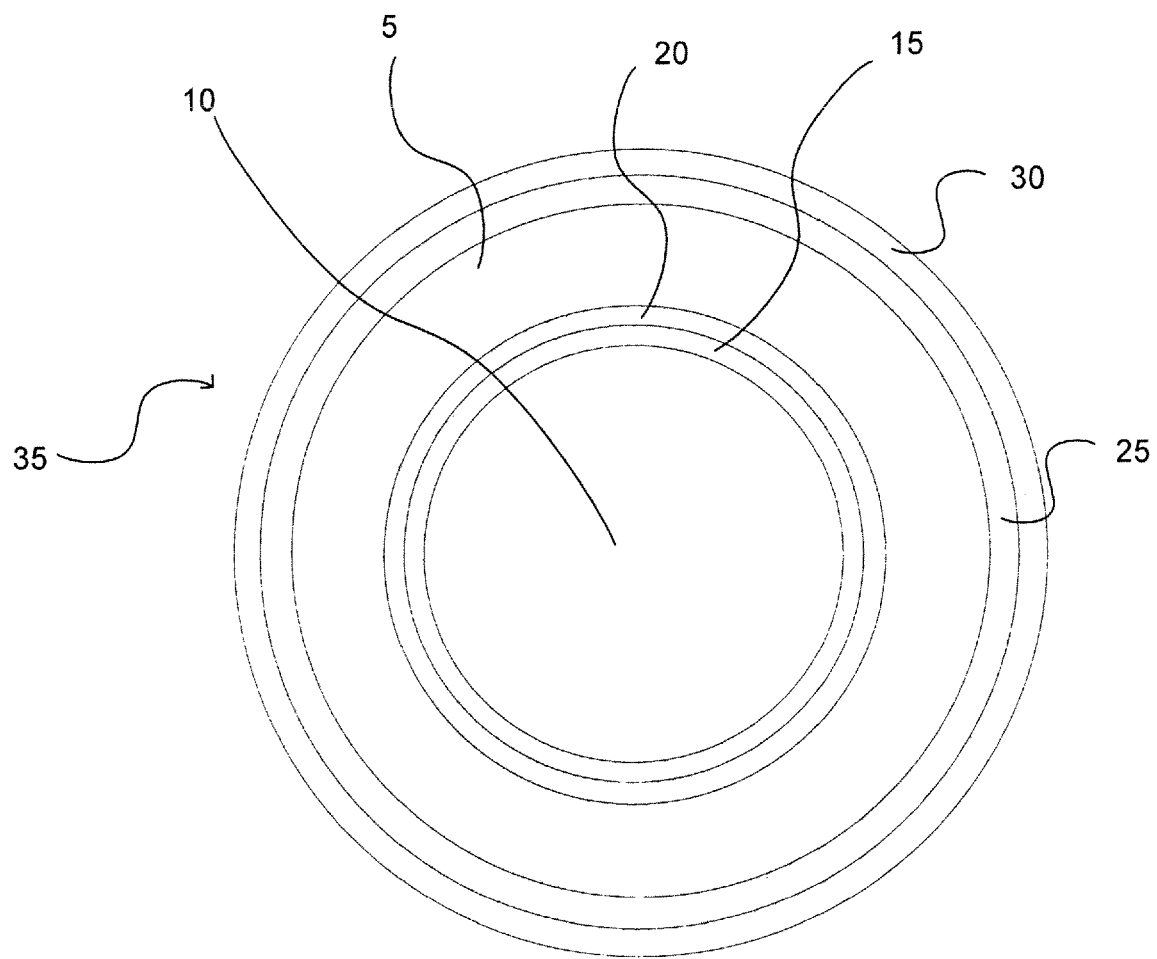
FIG. 8 is an illustration of a tubular medical device depicting an inner coating and an outer coating surrounding the device structure. In this embodiment, the device is depicted with multiple layers.

One embodiment of the invention is illustrated in FIG. 8, wherein the bioabsorbable medical device is a tubular structure comprising a body 5 having a lumen or a conduit 10. In this embodiment, there is provided an inner coating, comprising one or more layers, as shown in FIG. 8 as two layers 15 and 20, and an outer coating, which may comprise one or more layers, as shown in FIG. 8 as two layers 25, 30 on the surface of the medical device. For example, the inner coating may comprise at least two layers 15, 20 of a material which for example, can comprise an antibody layer 15 and a pharmaceutical composition 20 with or without a matrix. Multiple arrangement of layers can be deposited on either surface of the device and may contain different components or pharmaceutical substances or the layers can be the same. The outer coating 25, 30 surrounding the device structure can be the same or different in composition and can also comprise one or more pharmaceutical substance or composition depending on the need of the patient. In this embodiment, the device is depicted with multiple layers.

Figure 9:
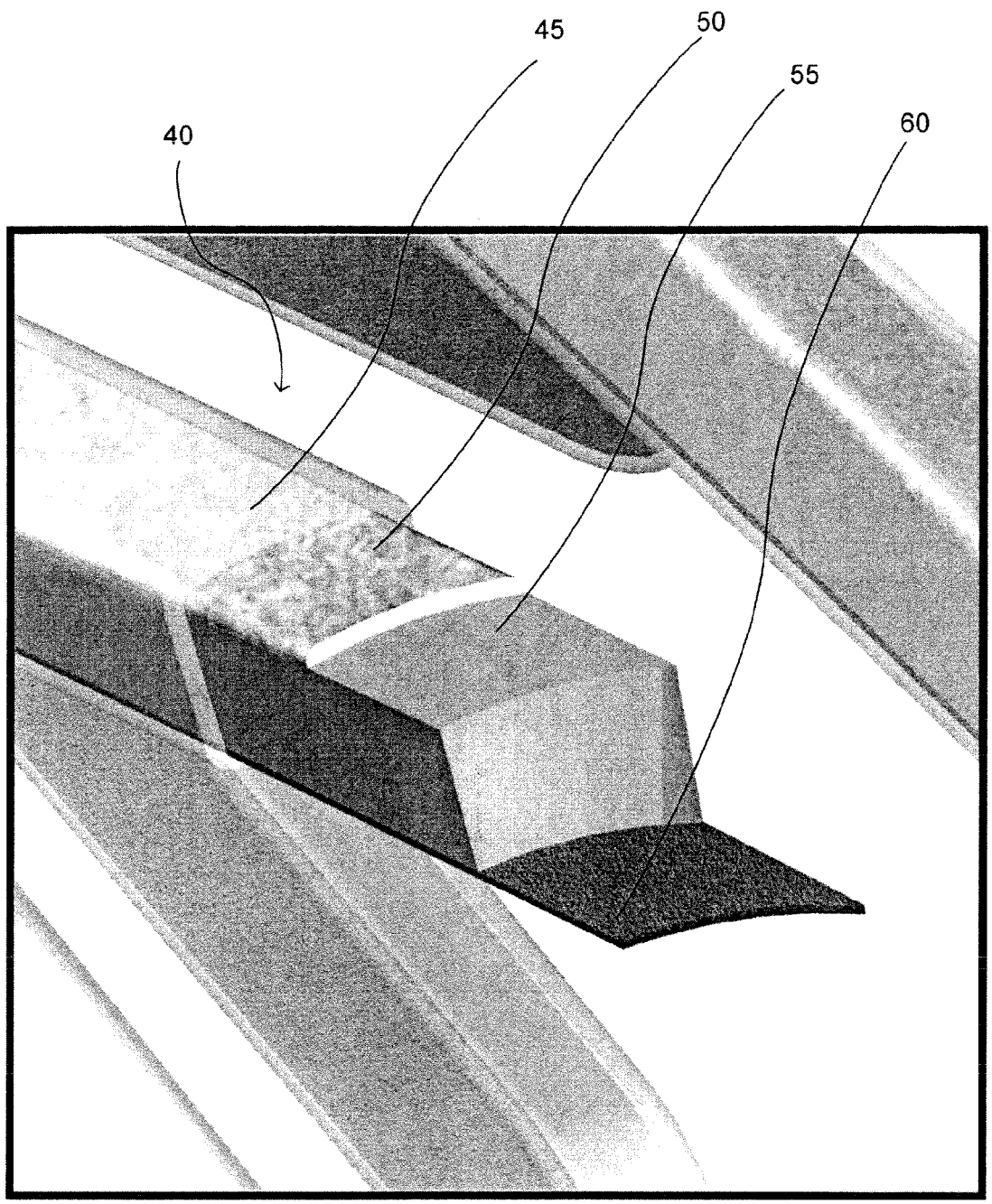
FIG. 9 is an illustration of a stent with a coating showing a perspective view of a stent strut with the layer in the outer surface and the inner, luminal surface with a coating.

FIG. 9 is an illustration of a stent with a coating showing a perspective view of a stent strut 55 with the layer in the outer surface and the inner with a coating with the outermost layer 45 depicting an antibody containing layer, an abluminal layer 50 comprising a biodegradable polymer with a drug load for release into the vessel wall, and the luminal coating 60 comprising a drug composition for release into the vessel surface after implantation. Spaces between the stent struts 40 are also depicted.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An implantable medical device, comprising a crystallized bioabsorbable polymer scaffold and a coating; said crystallized bioabsorbable polymer scaffold comprising, at least about 70% (w/w) of a base polymer comprising a poly (L-lactide) moiety, and/or a poly (D-lactide) moiety, and/or poly L-lactide-co-PEG moiety, and/or poly D-lactide-co PEG moiety, linked with a modifying copolymer comprising poly (L-lactide-co-Tri-methylene-carbonate) or poly (D-lactide-co-tri-methylene-carbonate) or poly (L-lactide-co-ε-caprolactone) or poly (D-lactide-co-ε-caprolactone) in the form of block copolymers or blocky random copolymers; and said coating comprising a bioabsorbable matrix and a ligand.

2. The implantable medical device of claim 1 wherein said ligand is configured to bind target cells in vivo.

3. The implantable medical device of claim 1 wherein said ligand is a small molecule, a peptide, an antibody, antibody fragments, or combinations thereof and the target cell is a progenitor endothelial cell antigen.

4. The implantable medical device of claim 1 wherein said coating comprises one or more layers.

5. The implantable medical device of claim 1 wherein said matrix comprises a naturally occurring or synthetic biodegradable polymer.

6. The implantable medical device of claim 5 wherein said matrix comprises at least one of the group consisting of: tropoelastin, elastin, laminin, fibronectin, fibrin, collagen, basement membrane proteins, and cross-linked tropoelastin.

7. The implantable medical device of claim 4 wherein at least one coating layer, or the implantable medical device itself, comprises a radioopaque or radio-detectable material.

8. The implantable medical device of claim 1 wherein said implantable medical device is impregnated with a pharmacological or biological substance.

9. The implantable medical device of claim 1 comprising a tube defining a lumen, said tube having an outer surface and an inner surface, said inner surface surrounding said lumen.

10. The implantable medical device of claim 9 wherein said outer surface is coated with a composition comprising a pharmacological substance.

11. The implantable medical device of claim 9 wherein said outer or inner surface is coated with a composition comprising a biological substance.

12. The implantable medical device of claim 8 or 10 wherein said pharmacological substance is at least one of the group consisting of: cyclosporin A, mycophenolic acid, mycophenolate mofetil acid, rapamycin, rapamycin derivatives, biolimus A9, CCI-779, RAD 001, AP23573, azathioprene, pimecrolimus, tacrolimus (FK506), tranilast, dexamethasone, corticosteroid, everolimus, retinoic acid, vitamin E, rosglitazone, simvastatins, fluvastatin, estrogen, 17.beta.-estradiol, hydrocortisone, acetaminophen, ibuprofen, naproxen, fluticasone, clobetasol, adalimumab, sulindac, dihydroepiandrosterone, testosterone, puerarin, platelet factor 4, basic fibroblast growth factor, fibronectin, butyric acid, butyric acid derivatives, paclitaxel, paclitaxel derivatives, LBM-642, deforolimus, and probucol.

13. The implantable medical device of claim 11 wherein said biological substance is at least one of the group consisting of: antibiotics/antimicrobials, antiproliferative agents, antineoplastic agents, antioxidants, endothelial cell growth factors, smooth muscle cell growth and/or migration inhibitors, thrombin inhibitors, immunosuppressive agents, antiplatelet aggregation agents, collagen synthesis inhibitors, therapeutic antibodies, nitric oxide donors, antisense oligonucleotides, wound healing agents, therapeutic gene transfer constructs, peptides, proteins, extracelluar matrix components, vasodialators, thrombolytics, anti-metabolites, growth factor agonists, antimitotics, steroids, steroidal antiinflammatory agents, chemokines, proliferator-activated receptor-gamma agonists, proliferator-activated receptor-alpha agonists proliferator-activated receptor-beta agonists, proliferator-activated receptor-alpha/beta agonists, proliferator-activated receptor-delta agonists, NF.kappa.beta., proliferator-activated receptor-alpha-gamma agonists, non-sterodial antiinflammatory agents, angiotensin converting enzyme(ACE) inhibitors, free radical scavangers, inhibitors of the CX3CR1 receptor and anti-cancer chemotherapeutic agents.

14. The implantable medical device of claim 1, the crystallized bioabsorbable polymer scaffold comprises a base polymer of from about 70% by weight of poly (L-lactide) with 30% by weight of modifying copolymer poly L-lactice-co-TMC.

15. A bioabsorbable implant comprising: a crystallized bioabsorbable polymer scaffold comprising at least about 70% (w/w) of a base polymer comprising a poly (L-lactide) moiety, and/or a poly (D-lactide) moiety, and/or poly L-lactide-co-PEG moiety, and/or poly D-lactide-co PEG moiety, linked with a modifying copolymer comprising poly (L-lactide-co-Tri-methylene-carbonate) or poly (D-lactide-co-tri-methylene-carbonate) or poly (L-lactide-co-ϵ-caprolactone) or poly (D-lactide-co-ϵ-caprolactone) in the form of block copolymers or blocky random copolymers; and a ligand.

16. The bioabsorbable implant of claim 15, wherein the base polymer is 70% by weight of poly L-lactide with 30% by weight of modifying copolymer poly L-lactice-co-TMC.

17. The bioabsorbable implant of claim 15, wherein the ligand comprises a small molecule, a peptide, an antibody, antibody fragments, or combinations thereof and the target cell is a progenitor endothelial cell.

18. The bioabsorbable implant of claim 17, wherein the antibody or antibody fragments is specific for binding a progenitor endothelial cell membrane antigen.

19. The bioabsorbable implant of claim 18, wherein the progenitor endothelial cell membrane antigen is selected from the group consisting of CD34, CD45, CD133, CD14, CDw90, CD117, HLA-DR, VEGFR-1, VEGFR-2, CD146, CD130, CD131, stem cell antigen, stem cell factor 1, Tie-2, MCH-H-2Kk and MCH-HLA-DR.

20. The implantable medical device of claim 1, wherein said medical device comprises a bioabsorbable implant having a tissue contacting surface and a fluid contacting surface, said implant comprising a bioabsorbable, biocompatible first coating for controlled release of one or more pharmaceutical substances from said tissue contacting surface, and a second coating comprising one or more ligands which bind to specific molecules on cell membranes of progenitor endothelial cells on the fluid contacting surface of the medical device.

21. The bioabsorbable implant of claim 20, wherein the medical device is a stent, a vascular or other synthetic graft, or a stent in combination with a synthetic graft.

22. The bioabsorbable implant of claim 20, wherein the medical device is a vascular stent.

23. The bioabsorbable implant of claim 20, wherein the tissue contacting surface coating comprises poly(DL-lactide-co-glycolide) and one or more pharmaceutical substances.

24. The bioabsorbable implant of claim 20, wherein the tissue contacting surface coating comprises poly(DL-lactide), or poly(lactide-co-glycolide), and paclitaxel.

25. The bioabsorbable implant of claim 20, wherein the pharmaceutical substance is at least one of the group consisting of antibiotics/antimicrobials, antiproliferative agents, antineoplastic agents, antioxidants, endothelial cell growth factors, smooth muscle cell growth and/or migration inhibitors, thrombin inhibitors, immunosuppressive agents, antiplatelet aggregation agents, collagen synthesis inhibitors, therapeutic antibodies, nitric oxide donors, antisense oligonucleotides, wound healing agents, therapeutic gene transfer constructs, peptides, proteins, extracellular matrix components, vasodialators, thrombolytics, anti-metabolites, growth factor agonists, antimitotics, steroids, steroidal antiinflammatory agents, chemokines, proliferator-activated receptor-gamma agonists, proliferator-activated receptor-alpha-gamma agonists, proliferator-activated receptor-alpha agonists, proliferator-activated receptor-beta agonists, proliferator-activated receptor-alpha/beta agonists, proliferator-activated receptor-delta agonists, NF.kappa.beta., nonsterodial antiinflammatory agents, angiotensin converting enzyme (ACE) inhibitors, free radical scavangers, inhibitors of the CX3CR1 receptor, and anti-cancer chemotherapeutic agents.

26. The bioabsorbable implant of claim 20, wherein the pharmaceutical substance is selected from the group consisting of cyclosporin A, mycophenolic acid, mycophenolate mofetil acid, rapamycin, rapamycin derivatives, biolimus A9, CCI-779, RAD 001, AP23573, azathioprene, pimecrolimus, tacrolimus (FK506), tranilast, dexamethasone, corticosteroid, everolimus, retinoic acid, vitamin E, rosglitazone, simvastatins, fluvastatin, estrogen, 17.beta.-estradiol, hydrocortisone, acetaminophen, ibuprofen, naproxen, fluticasone, clobetasol, adalimumab, sulindac, dihydroepiandrosterone, testosterone, puerarin, platelet factor 4, basic fibroblast growth factor, fibronectin, butyric acid, butyric acid derivatives, paclitaxel, paclitaxel derivatives, LBM-642, deforolimus, and probucol.

27. The bioabsorbable implant of claim 24, wherein the poly(DL-lactide) polymer comprises from about 50 to about 99% of the composition.

28. The bioabsorbable implant of claim 20, wherein either or both coatings comprise multiple layers of the poly(DL-lactide) polymer, poly(lactide-co-glycolide) copolymer, or mixture thereof.

29. The bioabsorbable implant of claim 20, wherein the either or both coatings comprise multiple layers of the pharmaceutical substances.

* * * * *